United States Patent
Mor (10) Patent No.: US 7,674,579 B2
(45) Date of Patent: Mar. 9, 2010

(54) APOPTOSIS-BASED EVALUATION OF CHEMOSENSITIVITY IN CANCER PATIENTS

(75) Inventor: Guillermo Mor, New Haven, CT (US)

(73) Assignee: Yale University, New Haven, CT (US)

( * ) Notice: Subject to any disclaimer, the term of this patent is extended or adjusted under 35 U.S.C. 154(b) by 180 days.

(21) Appl. No.: 10/580,170

(22) PCT Filed: Nov. 26, 2004

(86) PCT No.: PCT/US2004/039650

§ 371 (c)(1),
(2), (4) Date: May 24, 2007

(87) PCT Pub. No.: WO2005/054814

PCT Pub. Date: Jun. 16, 2005

(65) Prior Publication Data

US 2007/0275434 A1  Nov. 29, 2007

Related U.S. Application Data

(60) Provisional application No. 60/525,220, filed on Nov. 26, 2003.

(51) Int. Cl.
*C12Q 1/70* (2006.01)
*G01N 33/53* (2006.01)

(52) U.S. Cl. .......................... 435/5; 435/7.1

(58) Field of Classification Search .................... 435/5, 435/7.1
See application file for complete search history.

(56) References Cited

OTHER PUBLICATIONS

Cuello et al (Gynecol Oncol. Jun. 2001;81(3):380-90).*
Ofir et al., 2002, Taxol-Induced Apoptosis in Human SKOV3 Ovarian and MCF7 Breast Carcinoma Cells in Caspase-3 and Caspase-9 Independent, Cell Death and Differentiation, 9, 636-642.
Kolfschoten et al., 2002, Time-Dependent Changes in Factors Involved in the Apoptosis Process in Human Ovarian Cancer Cells as a Response to Cisplatin, Gynecologic Oncology, 84, 404-412.
Saito et al., 2004, Correlation Between Responsiveness of Neoadjuvant Chemotherapy and Apoptosis-Associated Proteins for Cervical Adenocarcinoma, Gynecologic Oncology, 92, 284-292.
Kamsteeg, et al., "Phenoxodiol—an isoflavone analog—induces apoptosis in chemoresistant ovarian cancer cells," Oncogene, 22(17), pp. 2611-2620, (May 1, 2003) XP002455201.
Flick, et al., "Apoptosis-based evaluation of chemosensitivity in ovarian cancer patients," Journal of Society of Gynecologic Investigation., 11(4), pp. 252-259, (May 4, 2004) XP009088472.
Supplementary European Search Report based on International Application No. PCT/US2004/039650, (Oct. 30, 2007).

* cited by examiner

*Primary Examiner*—Christopher H Yaen
(74) *Attorney, Agent, or Firm*—Cooley Godward Kronish LLP (57) ABSTRACT

Induction of apoptosis in target cells is a key mechanism by which chemotherapy induces cell killing. An in vitro system has been established for determining carboplatin and paclitaxel (Taxol) chemosensitivity of epithelial ovarian cancer cells, where measurements of caspase-3 activation are surrogate markers for activation of chemotherapy-induced programmed cell death. To validate the assay as a predictor of clinical chemotherapy-induced programmed cell death. To validate the assay as a predictor of clinical chemosensitivity in vitro apoptotic response were compared to the clinical response of the patients from whom the tumor cells were isolated. Caspase-3 activation in response to in vitro chemotherapy to both drugs was shown to have an 83% positive predictive value and a 71% negative predictive value. Markers of apoptosis such as caspase-3 activation can be quantitated and utilized to predict the clinical response to chemotherapy.

8 Claims, 4 Drawing Sheets

APOPTOSIS-BASED EVALUATION OF CHEMOSENSITIVITY IN CANCER PATIENTS

CROSS-REFERENCE TO RELATED APPLICATIONS

This application is a National Stage filing of International Application No. PCT/US2004/039650, filed on Nov. 26, 2004, which claims the benefit of U.S. Provisional Patent Application Ser. No. 60/525,220, filed Nov. 26, 2003, each of which is herein incorporated by reference in its entirety for all purposes.

STATEMENT REGARDING FEDERALLY-SPONSORED RESEARCH OR DEVELOPMENT

This work was supported by grants from the Ethyl F. Donaghue Foundation and by grants from the National Institutes of Health, RO1 HD37137-01A2 and R01CA92435-01. The U.S. government therefore has certain rights in the invention.

FIELD OF THE INVENTION

The invention is in the field of cancer therapies and prediction of tumor cell response to chemotherapeutic agents.

BACKGROUND OF THE INVENTION

Over 14,000 women in the U.S., each year die from epithelial ovarian carcinomas (1). Nearly 75% of patients present with advanced disease since, as of yet, no reliable means for early detection is available. The effective treatment of advanced or recurrent ovarian cancer is often compromised by both the intrinsic and acquired resistance of many ovarian carcinomas to one or more of the chemotherapeutic agents commonly employed in the treatment of this disease (2, 3). Without a practical means of predicting clinical response to therapeutic agents, treatment of any given patient is empirically based on the most successful agent or agents in a recent clinical trial rather than any objective assessment of individual tumor response. This is the functional equivalent of treating patients with septicemia with the combination of antibiotics found most effective in the treatment of such infections, without blood cultures and antibiotic testing of the cultured pathogens. While such an approach might be effective for a majority of patients many would die for lack of the appropriate antibiotic, which is the current situation for ovarian cancer and for that matter nearly all other solid tumors of adults.

To make treatment more effective, a number of assays have been proposed to help predict tumor cell responses to chemotherapeutic agents prior to treatment (2, 4-12). Various types of clonogenic assay have been used for many years to test cytotoxic compounds in vitro. Such assays are reasonably predictive of drug action in vivo and remain the standard against which other assays are compared but the best of them are not amenable to clinical situations given the low clonogenic efficiencies of most primary tumor samples in culture. Limited clinical success has been achieved in drug resistance studies performed on tumor tissue samples where a change in a metabolic parameter is measured after drug treatment as a surrogate for measurement of clonogenic survival (2, 4, 8, 13, 14). Assays for chemo-sensitivity such as ATP-TCA have shown promise in guiding the selection of suitable therapies on an individual basis (2, 9, 11, 15). Although not yet proven to be beneficial in prospective studies, results to date suggest that assays of surrogate markers of cell death could be effective tools to help guide the treatment of patients if the in vitro endpoint is actually a reasonable predictor of the in vivo response of the tumor from which the sample was obtained (16).

Resistance to programmed cell death (apoptosis) has been described as the "hallmark" of cancer transformation. The final effect of successful chemotherapy represents the consequences of the activation of the apoptotic machinery by the agents used: damage to DNA, microtubules and other cell components. Initially, the development of chemotherapeutic agents was based on the observation that tumor cells proliferate faster than normal cells which led to the original strategy of trying to, selectively if possible, block tumor cell DNA replication or cellular metabolism. At that time drug resistance was thought to arise from molecular changes inhibiting the drug/target interaction.

Caspases are highly specific proteases synthesized as zymogens and activated by cleavage which generates large and small subunits of the mature enzyme. Caspases can collaborate in the proteolytic cascade by activating themselves and each other (24, 25). Within these cascades, caspases can be divided into "initiator" caspases and downstream "effectors" of apoptosis. Initiator caspases, such as caspase-8 and 9, mediate their oligomerization and autoactivation in response to specific upstream signals. The effector caspases include caspases-3 and 7, which cleave cellular substrates and precipitate apoptotic death. (See, Human Caspase 3 nucleic acid (GenBank Accession NM_004346)[41]; Human Caspase 3 protein (GenBank Accession NP_004337)[42]; Human Caspase-7 nucleic acid (Caspase 7 nucleic acid, (GenBank Accession NM_0012227 (alpha), NM_033340 (beta), NM_033339 (gamma), NM_033338 (delta)); Human Caspase 7 protein (GenBank Accession NP_203125 (alpha), NP_203126 (beta), NP_203124 (delta))[43].

The elucidation of the detailed molecular mechanism of apoptosis and its function in normal physiology has resulted in a better understanding the effect of chemotherapy and the mechanisms of resistance. It is now well documented that the induction of apoptosis in target cells is a key mechanism for most anti-tumor therapies, including chemotherapy, radiation, immunotherapy and cytokines (17-22). More recently, studies have applied measurement of the apoptotic response to the determination of chemo-sensitivity (18). These studies indicate that drug-induced apoptosis but not antiproliferative measurement, can predict tumor response to chemotherapeutic drugs (23). Furthermore, the in vitro response of tumor cells exposed to physiological doses of chemotherapeutic agents can be tested for sensitivity or resistance by employing markers of apoptosis which correlate with tumor cell death.

Practical assays to predict the likelihood of individual tumor sensitivity and which optimize the potential for efficient treatment and avoid the toxicities of ineffective drugs are needed to facilitate the choice of adequate treatment.

SUMMARY OF THE INVENTION

The invention is directed to a method of predicting a clinical response of a tumor or a cancer cell to at least one chemotherapeutic agent in a patient comprising (a) contacting a sample comprising patient tumor or cancer cells with said agent in vitro and (b) detecting caspase-3 activity in the sample, thereby predicting a clinical response to said at least one chemotherapeutic agent.

DETAILED DESCRIPTION OF THE PREFERRED EMBODIMENTS

The invention is directed to a method of predicting a clinical response of a tumor or a cancer cell to at least one chemotherapeutic agent in a patient comprising (a) contacting a sample comprising patient tumor or cancer cells with said agent in vitro and (b) detecting caspase-3 activity in the sample, thereby predicting a clinical response to said at least one chemotherapeutic agent. In one embodiment, the predicting comprises detecting cell apoptosis. In another embodiment, the tumor cells are epithelial cells. In a preferred embodiment, the tumor cells are epithelial ovarian cancer cells.

In a different embodiment of the method of the invention, the cell sample is cultured from about 60-70% confluency before said contacting. In another embodiment, the sample is contacted with said at least one agent for a length of time from about 4 hours to about 48 hours. In a preferred embodiment the contacting is separate for each agent. In a highly preferred embodiment, the agents are selected from the group consisting of carboplatin, paclitaxel, docetaxel, gemcitabine, topoteca, cisplatin and any combination thereof. Other therapeutic agents may also be tested using the methods of the invention.

In addition, the invention is also directed to the method further comprising performing dose response measurements. In another embodiment, the method further comprises performing time course measurements. In a preferred embodiment, the tumor cells are primary tumor cells, ascites tumor cells or metastatic tumor cells.

The objective of this study was to determine whether an in vitro assay for apoptotic activity in response to chemotherapeutic drugs could be used to predict the in vivo patient response. Epithelial ovarian cancer cells (EOC) isolated from patients with ascites were treated in vitro with the commonly prescribed agents, carboplatin and paclitaxel (Taxol) and assayed for activation of caspase-3, an early marker of the apoptotic response. To establish the clinical application of in vitro apoptotic assays we compared the caspase-3 activity results with the clinical outcomes of the patients treated with the same drugs.

The following examples are illustrative of preferred embodiments of the invention and are not to be construed as limiting the invention thereto.

EXAMPLES

Methods

Cell Culture

Ovarian cancer cell lines HEY (gift from Dr. J M Trent, (26)), A2780 and CP70 (gifts from Dr. T C Hamilton, (27)) were cultured at 37° C. in a 5% CO2 atmosphere. Culture medium varied with the cell line: DME/F12 plus 1% calf serum (HEY); DME/F12 plus 10% FBS, 584 ug/ml L glutamine (A2780 and CP70). All formulations contained 100 µg/ml streptomycin, 62.5 µg/ml penicillin and 2.5 µg/ml amphotericin. Primary cells were cultured in 50% 199 media and 50% MCDB 105 media (Sigma), supplemented with 10% fetal bovine serum (Hyclone, South Logan, Utah), 10 mM HEPES, 0.1 mM MEM non-essential amino acids, 1 mM sodium pyruvate, 100 nM penicili/streptomycin (Gibco) and 4 ng/ml EGF (Sigma). For drug treatments, approximately $1 \times 10^5$ cells in exponential growth were sub-cultured in a 25 cm$^2$ flask per treatment. Carboplatin (Sigma C2538) or paclitaxel (Sigma T7402) was added to the media after the cells reached 60-70% confluence as described in the Results.

Patient Samples and Isolation of EOC Cells

With informed consent from 28 patients undergoing routine procedures at Yale-New Haven Hospital 100 to 200 ml of ascites fluid or pelvic washings were obtained. Epithelial cells were collected as previously described (28). Briefly, samples were centrifuged and the cellular pellet was resuspended in Hank's Balanced Salt Solution (HBSS; Gibco Invitrogen, Carlsbad, Calif.). The suspension was centrifuged at 1500 rpm for 10 mins at room temperature. The pellet was then resuspended in HBSS and layered onto LSM lymphocyte separation medium (ICN Biomedicals Inc, Aurora, Ill.) and centrifuged at 2000 rpm for 25 minutes at room temperature. The mononuclear cell-containing layer was collected and incubated with an anti-CD45 mAb conjugated to magnetic beads (Dynal, Oslo, Norway) at 4° C. with rotation for 30 minutes. Following this incubation, the cells were placed into a magnet and the unbound epithelial cells were collected, washed and placed into culture media. Purity of the epithelial ovarian cancer cells was 100% as determined by immunostaining for cytokeratin (Sigma). Remaining cells were cultured in primary culture medium as described above and evaluated for morphological evidence of malignancy by a pathologist. Viable, malignant cells were isolated from 21 of the 28 samples. In agreement with Lounis et al. (29), any fibroblastic cells in the isolated population disappeared after 2 to 3 passages and cells survived on average for 7 to 8 passages.

Nineteen of the 21 cases were ovarian cancer. Of the 19 ovarian cases, clinical diagnoses indicated 11 were Stage III and 5 were Stage IV epithelial ovarian tumors with varied histology: 11 papillary serous, 4 endometrioid type and 1 undifferentiated adenocarcinoma. The three additional cases were classified as ovarian cancers of borderline malignant potential (stage IC mucinous, stage IIIC serous with invasive implants and stage IIIS serous with micropapillary component).

Patients were monitored for disease recurrence based on physical symptoms, physical examination, CA-125 levels and radiologic imaging. Chemosensitivity is defined as no evidence of disease recurrence, based on the above monitoring, within 6 months of completing the chemotherapy regimen of carboplatin and paclitaxel. Sensitivity of six months is commonly used to define which patients are platinum-sensitive in order to direct second-line therapy (30). The majority of platinum-sensitive patients will respond to re-treatment with platinum based therapy while those patients that are platinum-resistant have much lower response rates with subsequent chemotherapy regimens (31).

Clonogenic Assays

Cells were seeded at 600 per 60 mm culture dish and incubated overnight to establish adherence then exposed to varying concentrations of drug for 4 hours. Medium was replaced and incubation was continued for 10-14 days. The cells were washed with 0.9% saline solution then fixed and stained in 72% methanol, 10% formaldehyde, 0.25% crystal violet. Colonies greater than 30 cells were counted. Percent survival was calculated based on the number of colonies in untreated dishes. Each treatment was done at least in duplicate.

TUNEL Assays (Terminal Deoxynucleotidyl Transferase-Mediated dUTP-biotin Nick End Labeling)

To avoid loss of the apoptotic cells, which detach from monolayer culture and are washed away, cells were cultured in suspension above a one ml layer of 1% agarose per well of a 6-well plate. Two ml of cells at $1\times10^5$/ml growth medium were placed in each well and incubated at 37° C. with 5% $CO_2$. Plates were agitated gently once per day. After drug exposure for 4 hr, the cells were centrifuged, resuspended in fresh medium and returned to the same wells for 48 hr. Cells were centrifuged at 1000 rpm for 10 min, resuspended in 0.5 ml 10% neutral buffered formalin and incubated at room temperature for 10 min. Centrifugation was repeated and cells were resuspended in 80% ethanol. A 25 µl aliquot was pipeted onto a glass slide and dried at room temperature until no moisture was evident. Cells were calorimetrically stained with TUNEL assay reagents (Trevigen) according to the protocol provided by the manufacturer.

Caspase-3 Assay

After drug treatment, cells were lysed and collected in cold 10 mM Tris, pH 7.5, 10 mM Na Phosphate buffer, 130 mM NaCl, 1% Triton X-100, 10 mM Na Pyrophosphate plus freshly added Protease Inhibitor Cocktail (20 µl/ml, Sigma P8340) and 2 MM PMSF. Lysates were incubated on ice for 30 min, mixing every 5 min by gentle vortexing. Debris was pelleted by centrifugation at 4° C., >10,000×g for 5 min. Supernatants were frozen and stored at −70° C. Protein concentration was determined by BioRad Protein Assay (Bio-Rad).

Caspase-3 activity was measured in duplicate from 50 µg cell lysate samples (lysate comprised less than 20% of the total reaction volume)(Promega Corp. CaspACE™ Assay System, Colorimetric). Briefly, caspase-3 substrate (Ac-DEVD-pNA) was added to a final concentration of 200 µM in 100 µl reactions containing 100 nM HEPES, pH 7.5, 10% sucrose, 0.1% CHAPS, 2% DMSO, and 10 mM DTT in a 96 well plate. Plates were incubated at 37° C. for 4 hr. Absorbance of the cleaved product was read at 405 nm in a Dynatech MR3000 plate reader. Blank values were subtracted and caspase-3 activity was expressed as the absorbance at 405 nm of the cleaved substrate (pNA). Drug treated samples were compared with samples which had not been treated to give a value called relative activity.

SDS PAGE and Western Blots

Cells were treated with drug as described above. Cells were then scraped from the culture vessel, pelleted at 2000 rpm at room temperature and lysed in phosphate buffered saline with 1% NP40, 0.1% sodium dodecyl sulfate. After 20 min on ice, debris was removed by centrifugation at 14,000×g at 4° C.

Protein concentration was determined and 20 µg samples were denatured in sample buffer (2.5% SDS, 10% glycerol, 5% b-mercaptoethanol, 0.15 M Tris (pH 6.8) and 0.01% broinophenol blue) and subjected to 10 or 12% SDS-PAGE. Proteins were transferred to PVDF membranes (Immobilon, Millipore, Bedford, Mass.) at 100V for 105 min.

Western blots were performed as previously described (32) (28). Antibodies and concentrations were: rabbit anti-actin (Sigma, 1:10,000), rabbit anti-proform caspase-3 (Santa Cruz, Santa Cruz Calif. 1:1000), rabbit anti-cleaved-caspase-3 (CellSignaling, 1:1000). Antibody binding was determined by enhanced chemiluminescence detection of peroxidase conjugated secondary antibodies (Vector).

Results

Clonogenic Assays

Clonogenic or colony-forming assays are one of the most established and reliable methods for assessment of survival and sensitivity to drugs. Colony-forming assays were performed on several ovarian cell lines including A2780 previously isolated from an ovarian cancer patient and shown to be sensitive to platinum-based therapies (27, 33) and the CP70 cell line subcloned from A2780 cells by selection for high resistance to platinum compounds (27, 33). IC50's were calculated as shown in Table 1. In agreement with previous studies, CP70 is about 25-fold more resistant to carboplatin than A2780 (27, 33). Response to paclitaxel demonstrates that HEY cells are the most resistant and CP70 cells are the most sensitive.

Optimization of Drug Treatment for Caspase-3 Assays

Figure 1:
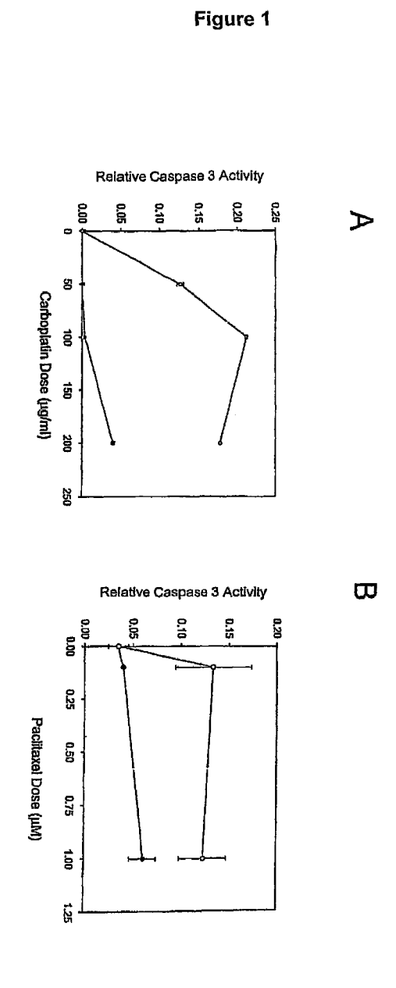
FIGS. 1A-B. Dose response and time course for caspase-3 activation by carboplatin and paclitaxel. After treatment with carboplatin or paclitaxel, caspase-3 activity in cell extracts was measured in duplicate as described in Methods. Panel A: A2780 cells were treated with varying concentrations of carboplatin for 24 and 48 hrs. Error bars represent SE from 2 independent experiments. Closed circles—24 hr treatment, open circles—48 hr. Panel B: CP70 cells were treated with varying concentrations of paclitaxel for 16 and 30 hr. Error bars represent SE from 3 independent experiments. Closed circles—16 hr treatment, open circles—30 hr.

Caspase-3, one of the effector caspases, is a key enzyme in the apoptotic cascade and is activated by either caspase 8 or caspase 9 through signaling by the death receptors (Fas/FasL system) or by the mitochondria respectively. Thus, all apoptotic activity is triggered by activation of caspase-3 (34). Ovarian carcinoma cell lines A2780 and the platinum resistant variant clone CP70 were assayed for caspase-3 activity after treatment with either carboplatin or paclitaxel. In order to optimize treatment conditions, both dose response and time course measurements were performed (FIG. 1). In the carboplatin sensitive cell line A2780, significant caspase-3 activity was observed after 24 hour exposure to the drug. Optimal activity was obtained after 48 hour treatment with carboplatin at a dose of 100 µg/ml (FIG. 1A). CP70 cells were the most sensitive to paclitaxel and therefore used for dose response and time course optimization. FIG. 1B shows that significant caspase-3 activity was observed in CP70 cells at a dose of 0.1 µM and 30 hours treatment. For further assays, doses of 0.1 and 1 µM paclitaxel for 30 hours and 50 and 100 µg/ml carboplatin for 48 hours were adopted as the standard treatment conditions.

Figure 2:
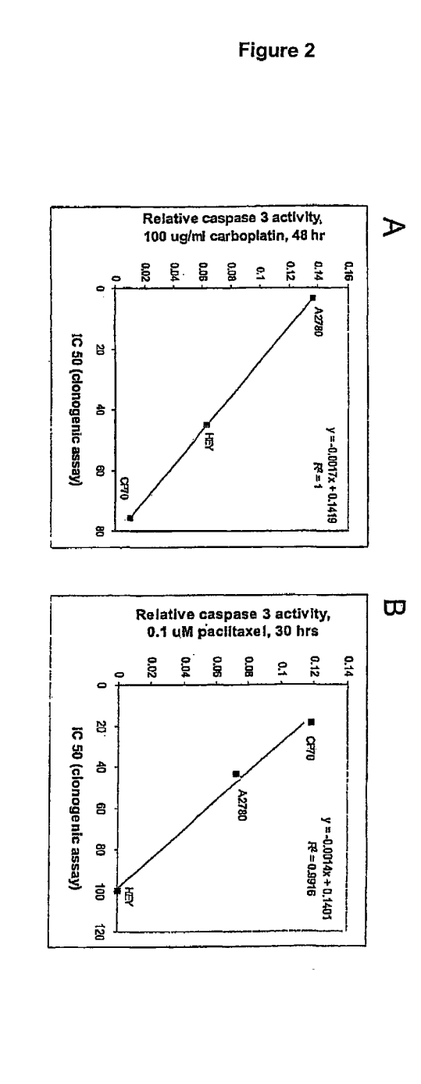
FIGS. 2A-B. Correlation of relative caspase-3 activity and clonogenic assay. The IC-50 concentrations for each ovarian cancer cell line, for each drug, calculated from survival curves in the clonogenic assays were plotted against the relative caspase-3 activities measured after drug treatments under the conditions adopted as optimal standards. Panel A: Caspase-3 activity after 48 hr exposure to 100 µg/ml carboplatin. Panel B: Caspase-3 activity after 30 hr. exposure to 0.1 µM paclitaxel.

Caspase-3 activity (absorbance at 405 nm of the substrate cleavage product, pNA) after 0.1 mM paclitaxel (30 hr) or 100 µg/ml carboplatin (48 hr) was compared with the results (IC50 values) from the clonogenic assays. The correlation of the two sets of data is shown in FIG. 2. Comparison of the IC50 values and the caspase-3 activities showed a positive correlation in both cases (FIG. 2A: carboplatin, 2B: paclitaxel). The standard conditions clearly distinguish the different sensitivities of the three cell lines as well as the clonogenic assay. Since clonogenicity is considered a valid assessment of drug sensitivity we concluded that measurement of the apoptotic response via caspase-3 activity was a reasonable and more rapid alternative.

Caspase-3 Assays and Apoptotic Response

We then evaluated caspase-3 activity in primary cultures of ovarian cancer cells isolated from malignant ovarian ascites. Cells that showed an increased caspase-3 activity relative to untreated control samples were considered sensitive to the drug. Twelve of 22 cultures were resistant to paclitaxel-induced apoptosis since no caspase-3 activity was detected. Ten were sensitive to paclitaxel as shown by a significant increase in caspase-3 activity following paclitaxel treatment. On the other hand, 21 out of 22 cases were sensitive to carboplatin; only one did not show a response (Table 2).

TUNEL Assays

Figure 3:
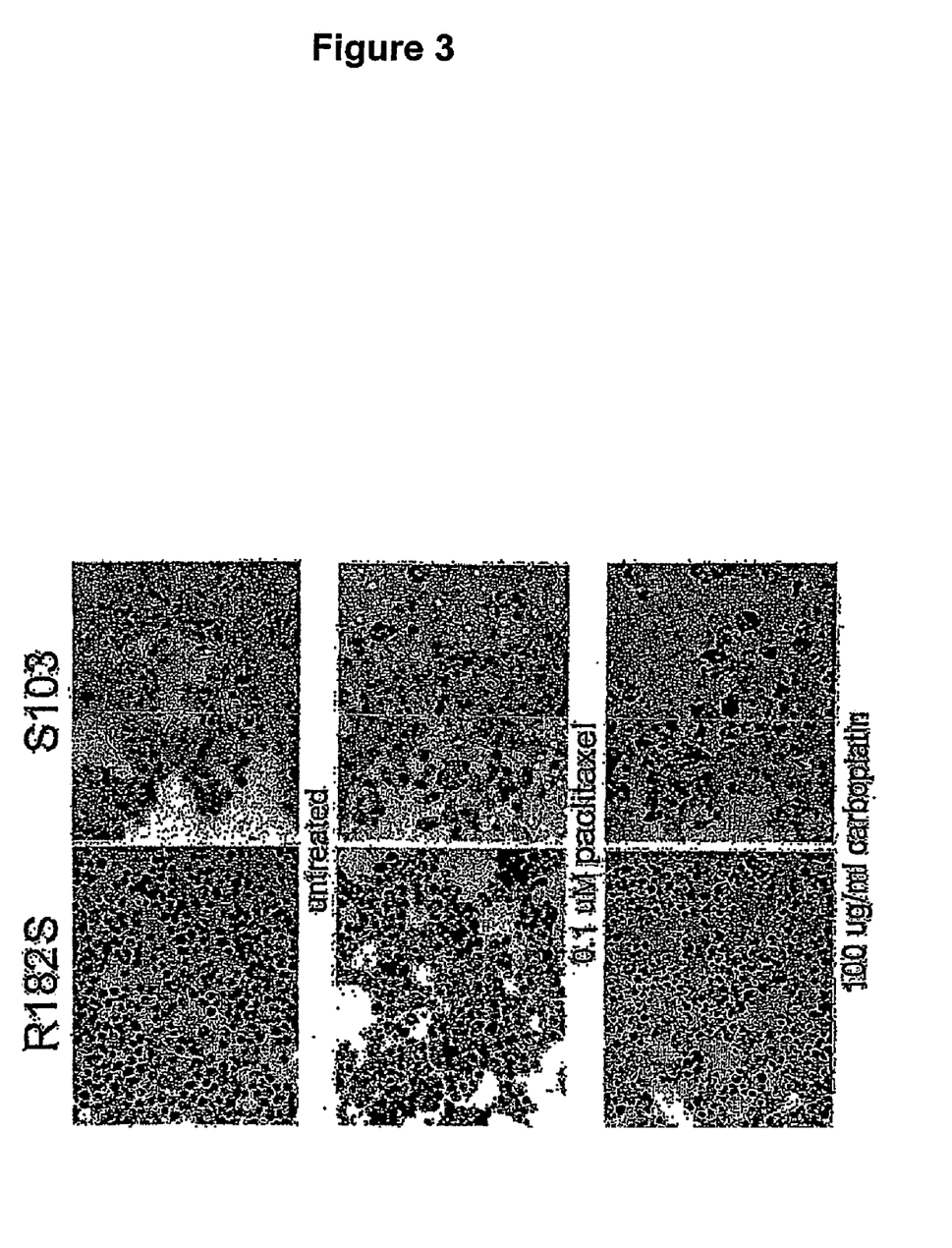
FIG. 3. Apoptotic response to carboplatin and paclitaxel visualized by TUNEL assay. Ovarian tumor cells cultured from ascites samples of ovarian cancer patients and treated in vitro with carboplatin and paclitaxel as described in Methods were collected, fixed and dried onto coated slides. Cells were permeabilized and a colorimetric TUNEL assay performed as described in Methods. Note: Sample R182S is distinct from patient sample R182 shown in FIG. 4 western blots.

In order to correlate caspase-3 activation and apoptosis, TUNEL assays was performed in EOC cells following in vitro treatment with chemotherapy. EOC cells RI82S and 5103 were treated with carboplatin and paclitaxel and stained for labeling of DNA ends (FIG. 3). Treatment with 0.1 µM paclitaxel induces a 30-40% increase in number of TUNEL-positive RI 82S cells and 10-20% of S 103 cells compared to the untreated controls. However, treatment with 100 µg/ml carboplatin induces a much larger percentage of RI 82S TUNEL-positive cells (90%) and 30.40% of S 103 cells treated in the same way stain for apoptosis.

Western Blot Analysis for Caspase-3 Activation

Figure 4:
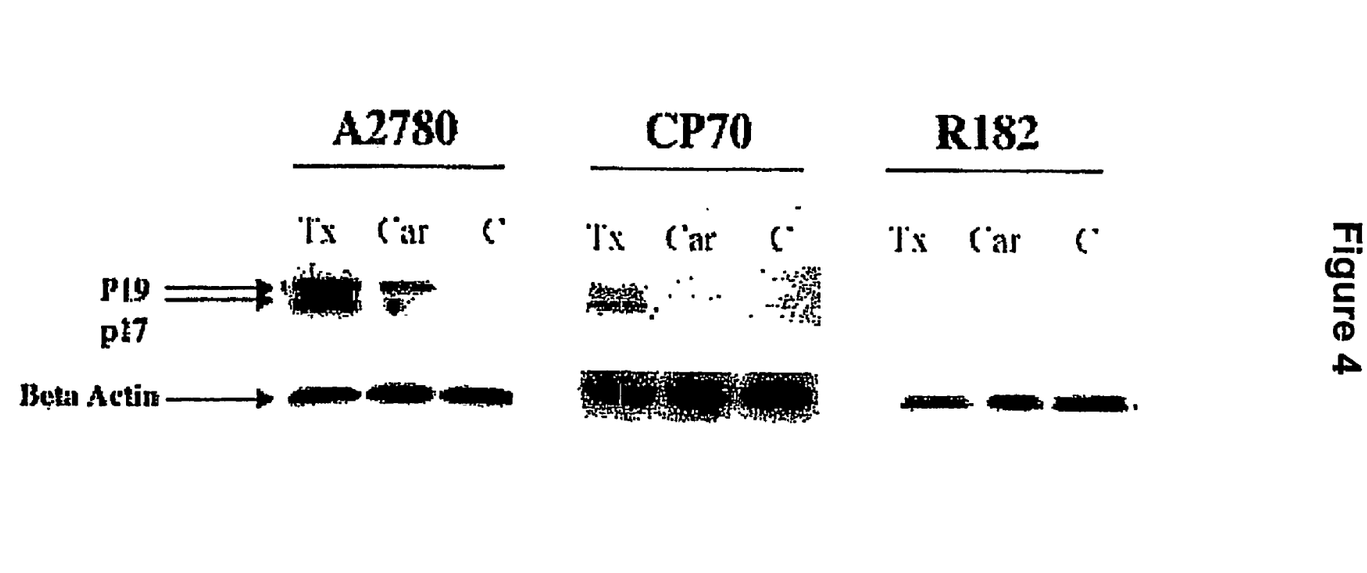
FIG. 4. Western blots for activated caspase-3. The expression of the active forms (p19 and p17) of caspase-3 was determined in ovarian cancer cells following treatment with either carboplatin (Car) or paclitaxel (Tx). p19 and p17 are expressed only in the chemosensitive cells but not in the resistant or in the control (untreated). Beta actin indicates the presence of protein in all the groups. The figure is representative of at least three independent experiments.

The presence of the active forms of caspase-3 in EOS cells in response to carboplatin and paclitaxel was evaluated by Western blot analysis. FIG. 4 shows representative results for A2780, CP70 and EOC R182, cells that showed dramatically different responses to carboplatin and paclitaxel in the enzyme assay. Active forms of caspase-3 are absent from the untreated controls. Treatment of CP70 cells (paclitaxel sensitive) with 0.1 µM paclitaxel for 30 hr induces the expression of the active forms of caspase-3, while the same treatment of EOC R182 cells (paclitaxel resistant) shows no expression of caspase-3 active forms. No active forms of caspase-3 are present after treatment of CP70 and EOC 8182 (both carboplatin resistant) with 100 µg/ml carboplatin for 48 hr. In addition, the carboplatin and paclitaxel sensitive A2780 ovarian cancer cells express high levels of the p21 and p17 caspase-3 active forms in response to paclitaxel treatment and moderate levels of caspase-3 active forms in response to carboplatin. These results are in agreement with the colorimetric enzymatic activity assay.

Comparison of In Vitro Response to Clinical Response

A blinded evaluation of patient clinical data revealed that of the 16 cases of invasive ovarian carcinoma 13 of these patients had been treated with carboplatin and paclitaxel and had sufficient time to determine in vivo drug response. Chemotherapy sensitivity was defined as no evidence of disease recurrence for 6 months following the completion of the chemotherapy regimen. Of seven patients who were clinically responsive (chemo-sensitive) five isolated cell samples responded in vitro to both drugs, while two responded to only one or neither of the two agents. Of six patients who were chemo-resistant, five were in the category of response to only one or neither drug (Table 3). Based on these results measurement of caspase-3 activation in response to in vitro chemotherapy has a 77% overall predictability to the clinical course, an 83% positive predictive value and a 71% negative predictive value with 71% sensitivity and 83% specificity. It is noteworthy that three of the five patients that were correctly predicted to be sensitive to the carboplatin and paclitaxel regimen had been followed for greater than 12 months. Two of these patients are without evidence of disease at 12 and 26 months while the third patient recurred at 23 months. The other two patients had been followed for six to nine months as of this writing, with no recurrence.

Discussion

A growing body of evidence suggests that tumor regression or disappearance after effective chemotherapy or radiation therapy is the result of the ability of the therapeutic agent to induce apoptosis in tumor cells and resistance to various therapies may be due to defects in the apoptotic response (reviewed in (22)). In the present study we show a positive correlation between the clinical response of ovarian cancer patients and the evaluation of caspase-3 activity of tumor cells in response to in vitro chemotherapy. Our better understanding of the molecular mechanism of apoptosis and its function in normal physiology has resulted in a better understanding of the effects of chemotherapy and the mechanisms of resistance. It is now well documented that the induction of apoptosis in target cells is a key mechanism for most antitumor therapies, including chemotherapy, -radiation, immunotherapy and cytokines. The realization that apoptosis is a key factor that contributes to the anti-tumor activity of chemotherapeutic drugs has allowed us to rethink how drug resistance may arise and look for new approaches to evaluate the tumor response to chemotherapy.

We hypothesized that the in vitro apoptotic response to chemotherapeutic drugs should correlate with the clinical response of patients treated with these agents and that an assay to measure this sensitivity should be able to predict the efficacy of treatment before it is administered. To test this hypothesis, we have determined optimal conditions for drug treatment of cultured epithelial ovarian cancer cells which produced a quantitative apoptotic response in sensitive cells and which showed a correlation to the results of clonogenic assays in which the cells were treated with the same drugs. These conditions were then applied in the in vitro treatment of EOC cell preparations from malignant ascites patient samples. Comparisons with clinical response in those cases where the patients were treated with the same drugs suggest that in vitro results are potentially predictive of in vivo response.

This approach assumes that the cells isolated from the ascitic fluid are representative of the tumor. Previous studies found that cultured malignant ascites cells express the same antigens and contain the same genetic markers as the primary tumor and—concluded that these cells are an accurate representation of the original tumor (29, 35, 36). Furthermore, many if not all, ovarian cancer cell lines have been derived from cells isolated from the ascitic fluid of ovarian cancer patients.

The in vitro colony assay proved highly correlative to in vivo anticancer drug sensitivity and resistance for ovarian cancer and myeloma (37). Although levels of expression of the various factors involved in apoptotic responses such as p53, bax, bcl-2 have not been predictive of response to chemotherapy (38), the actual measurement of apoptosis in response to therapy has been more promising (39). Gibb et al. have shown that apoptosis correlates with the sensitivity of ovarian cancer cell lines to both cisplatin and paclitaxel (18). We therefore based our optimization of drug-induced apoptosis measurement on the in vitro colony assay. For measurement of the apoptotic response we choose to measure the activation of caspase-3 which has been shown to be one of the crucial steps in the apoptotic response (34, 40).

Under the optimized conditions used for dose and time of treatment, our results show a positive correlation of caspase-3 activity with the LD50 data obtained from colony assays (R=1 and 0.99 respectively for carboplatin and paclitaxel). Therefore we concluded that caspase-3 activity from ovarian tumor cells treated with antineoplastic agents in vitro should be as effective as the colony assay in predicting the chemosensitivity of ovarian tumors in vivo. Indeed, in our experiments using caspase-3 as a marker of sensitivity to chemotherapy a positive correlation to clinical response was found. However, this correlation is evident only when we take into consideration the separate in vitro responses to both carboplatin and paclitaxel. No attempt was made to treat cells in vitro simultaneously with both agents. Thus, this study suggests the importance of analyzing more than one factor in order to obtain the proper correlation. This is completely different from previous attempts by others to employ in vitro assays for chemosensitivity that have tried to correlate single drug responses to clinical response. Pending sufficient time for clinical follow-up and instituting a prospective protocol using this analysis, more cases will be added to confirm this evaluation as well as assess any benefit to long term survival.

TUNEL analysis of a few cases further confirmed full apoptotic morphology in response to the drugs. Western blot analysis performed on select samples confirmed the caspase-3 activity assays. And in two cases we were able to perform a clonogenic assay on cells isolated from patient ascites samples treated with carboplatin (not shown) which also confirmed the results of the caspase-3 assays.

Practical assays to predict the likelihood of individual tumor sensitivity are needed and would permit the choice of agents to which the patients' tumors are most sensitive. In this study we chose to evaluate the treatment of carboplatin and paclitaxel since this combination has become the internationally accepted regimen for the initial treatment of epithelial ovarian cancer. The same method could be used to predict the effectiveness of other treatment regimens. The ability to predict which chemotherapy combination will have the greatest efficacy in a first line therapy will optimize the potential to achieve long term remission or cure in ovarian cancer patients. Patients could avoid treatment with drugs to which their tumor is resistant, thus saving time and the toxicity of ineffective therapy. Such an assay, once optimized and shown to reflect actual tumor response in vivo, will allow clinicians to select the best drug(s) to treat an individual's tumor and avoid the toxicities of drugs to which her tumor is resistant. Measurement of caspase-3 activity in response to anticancer therapies, easily performed in a well-equipped clinical laboratory, is a practical equivalent to the colony assay and can be applied to cancer cells isolated from the malignant ascites fluid of ovarian cancer patients to predict their response to proposed treatment regimens.

REFERENCES

1. Jemal, A., Murray, T., Samuels, A., Ghafoor, A., Ward, E., and Thun, M. J. Cancer Statistics, 2003. CA: Cancer J Clin, 53: 5-26, 2003.
2. Sevin, B.-U., and Perras, J. Tumor heterogeneity and in vitro chemosensitivity testing in ovarian cancer. Amer J Obstet Gynecol, 176. 759-766, 1997.
3. Cheng, J. Q., Jiang, X., Fraser, M., Li, M., Dan, H. C., Sun, M., and Tsang, B. K. Role of X-linked inhibitor of apoptosis protein in chemoresistance in ovarian cancer: possible involvement of the phosphoinositide-3 kinase/Akt pathway. Drug Resist Updat, 5: 131146, 2002.
4. Ness, R., Wisniewski, S., Eng, H., and Christopherson, W. Cell viability assay for drug testing in ovarian cancer: in vitro kill versus clinical response. Anticancer Research, 22: 1145-1149, 2002.
5. Fanning, J., Biddle, W., Glodrosen, M., Crickard, K., Crickard, U., Piver, M., and Foon, K. Comparison of cisplatin and carboplatin cytotoxicity in human ovarian cancer cell lines using the MTT assay. Gynecol Oncol, 39: 119-122, 1990.
6. Suoaio, e., Lipponen, P., Maenpaa, J., Syrjanen, K., Kangas, L., and Tuomisto, L. Mitotic index in the subrenal capsule assay as an indicator of the chemosensitivity of ovarian cancer. Cancer Chemother Pharmacol, 41: 15-21, 1997.
7. Eltabbakh, G., Piver, M., Hempling, R., Recio, F., Lele, S., Marchetti, D., Baker, T., and Blumenson, L. Correlation between extreme drug resistance assay and response to primary paclitaxel and cisplatin in patients with epithelial ovarian cancer. Gynecol Oncol, 70: 392-397, 1998.
8. S. Orr, J., Orr, P., and Kern, D. Cost-effective treatment of women with advanced ovarian cancer by cytoreductive surgery and chemotherapy directed by an in vitro assay for drug resistance. Cancer J Sci Am, 5. 174-178, 1999.
9. Konecny, G., Crohns, C., Pegram, M., Felber, M., Lude, S., Kurbacher, C., Cree, I., Hepp, H., and Untch, M. Correlation of drug response with the ATP tumor chemosensitivity assay in primary FIGO stage III ovarian cancer. Gynecol. Oncol., 77: 258-263, 2000.
10. Taylor, C., Sargent, J., Elgie, A., C J, W., Lewandowicz, G., Chappatte, O, and Hill, J. Chemmosensitivity testing predicts survival in ovarian cancer. Eur J Gynaecol Oncol, 22: 278-282, 2001.
11. Breidenbach, M., Rein, D., Mallmann, P., and Kurbacher, C. Individualized long-term chemotherapy for recurrent ovarian cancer after failing high-dose treatment. Anticancer Drugs, 13: 173-176, 2002.
12. Taylor, C., Sargent, J., Elgie, A., Reid, F., Alton, P., and Hill, J. The clinical relevance of chemosensitivity testing in ovarian cancer. Cancer Detect Prev, 22: 305-312, 1998.
13. Baguley, B., Marshall, E., Whittaker, J., Dotchin, M., Nixon; J., McCrystal, M., Finlay, G., Matthews, J., Holdaway, K., and VanZijl, P. Resistance mechanisms determining the in vitro sensitivity to paclitaxel of tumour cells cultured from patients with ovarian cancer. Eur J Cancer, 31A: 230-237, 1995.
14. Coley, H. M. Drug resistance studies using fresh human ovarian carcinoma and soft tissue sarcoma samples. Keio J Med, 46: 142-147, 1997.
15. Kurbacher, C., Mallmann, P., Kurbacher, J., Hubner, H., and Krebs, D. Chemosensitivity testing in gynecologic oncology. Experiences with an ATP bioluminexcence assay. Geburtshilfe Frauenheilkd, 56: 70-78, 1996.

16. Cortazar, P., and Johnson, B. E. Review of the efficacy of individualized chemotherapy selected by in vitro drug sensitivity testing for patients with cancer. J. Clinical Oncol., -17: 1625-1631, 1999.

17. Henkels, K., and Turchi, J. Induction of apoptisis in cisplatin-sensitive and -resistant w human ovarian cancer cell lines. Cancer Res, 57: 4488-4492, 1997.

18. Gibb, R., Taylor, D., Wan, T., O'Connor, D., Doering, D., and Gercel-Taylor, C., Apoptosis as a measure of chemosensitivity to cisplatin and taxol therapy in ovarian cancer cell lines. Gynecol Oncol, 65: 13-22, 1997.

19. Hannun, Y. Apoptosis and the dilemma of cancer chemotherapy. Blood, 89: 1845-1853, 1997.

20. Fisher, D. Apoptosis in cancer therapy: crossing the threshold. Cell, 78: 539-542, 1994.

21. Hickman, J. Apoptosis induced by anticancer drugs. Cancer Metastasis Rev, 11: 121-139, 1992.

22. Johnstone, R., Ruefli, A., and Lowe, S. Apoptosis: a link between cancer genetics and chemotherapy. Cell, 108: 153-164, 2002.

23. Caserini, C., Pratesi, G., Tortoreto, M., Bedogne, B., Carenini, N., Supino, R., Perego, P., Righetti, S., and Zunino, F. Apoptosis as a determinant of tumor sensitivity to topotecan in human ovarian tumors: preclinical in vitro/in vivo. Clin Cancer Res, 3: 955-961, 1997.

24. Cohen, G. M. Caspases: the executioners of apoptosis. Biochem. J., 326 (Pt 1): 1-16, 1997.

25. Cain, K., Bratton, S. B., and Cohen, G. M. The Apaf-1 apoptosome: a large caspase activating complex. Biochem, 9: 203-214, 2002.

26. Buick R., Pullano, R., and Trent, J. Comparative properties of five human ovarian adenocarcinoma cell lines. Cancer Res, 45: 3668-3676, 1985.

27. Behrens, B., Hamilton, T., Masuda, H., Grotzinger, K., Whang-Peng, J., Louie, K, Knutsen, T., McKoy, W., Young, R., and Ozols, R. Characterization of a cisdiammine dichloroplatinunn(II)-resistant human ovarian cancer cell line and its use in evaluation of platinum analogues. Cancer Res, 47: 414-418, 1987.

28. Kamsteeg, M., Rutherford, T., Sapi, E., Hanczaruk B., Shahabi, S., Flick M., Brown, D., and Mar, G. Phenoxodiol. An isoflavone analogue-induces apoptosis in chemoresistant ovarian cancer cells. Oncogene, 22: 2611-2620, 2003.

29. Lounis, H., Provencher, K., Godbout C., Fink, K., Milot, M.-J., and Mes-Masson, A.-M. Primary cultures of normal and tumoral human ovarian epithelium: a powerful tool for basic molecular studies. Exp. Cell Res., 215: 303-309, 1994.

30. Markman, M., and Hoskins, W. Responses to salvage chemotherapy in ovarian cancer: a critical need for precise definitions of the treated population. J. of Clinical Oncology, 10: 513-514, 1992.

31. Markman, M., and Bookman, M. A. Second-line treatment of ovarian cancer. Oncologist, 5: 26-35, 2000.

32. Song, J., Sapi, E., Brown, W., Nilsen, J., Tartaro, K., Kacinski, B., Craft, J., Naftolin, F., and Mor, G. Roles of Fas and Fas ligand during mammary gland remodeling. J Clinical Investig, 106: 1209-1220, 2000.

33. Perez, R., Perez, K., Handel, L., and T C, H. In vitro interactions between platinum analogues in human ovarian-carcinoma cell lines. Cancer Chemother Pharmacol, 29: 430-434, 1992.

34. Jdnicke, R., Sprengart, M., Wati, M., and Porter, A. Caspase-3 is required for DNA fragmentation and morphological changes associated with apoptosis. J Biol Chem, 273: 9357-9360, 1998.

35. Provencher, D., Finstad, C., Saigo, P., Rubin, S., Hoskins, W., Federici, M., Stockert, E., Lloyd, K., and Lewis, J. Comparison of antigen expression on fresh and cultured ascites cells and on solid tumors of patients with epithelial ovarian cancer. Gynecol Onc, 50: 7883, 1993.

36. Metcalf, K., Selby, P., Trejdosiewicz, L., and Southgate, J. Culture of ascitic ovarian cancer cells as a clinically-relevant ex vivo model for the assessment of biological therapies. Eur J Gynaecol Oncol, 19: 113-119, 1998.

37. Salmon, S., Hamburger, A., Soelmlen, B., Durie, B., Alberts, D., and Moon, T. Quantitation of differential sensitivity of human-tumor stem cells to anticancer drugs. N Engl J Med, 298: 1321-1327, 1978.

38. Sjostrom, J., Blomqvist, C., von Boguslawski, K., Bengtsson, N., Mjaaland, I., Malmstrom, P., Ostenstadt, B., Wist, B., Valvere, V., Takayama, S., Reed, J., and Saksela, E. The predictive value of bcl-2, bax, bcl-xL, bag-1, fas and fasL for chemotherapy response in advanced breast cancer. Clin Cancer Res, 8: 811-816, 2002.

39. Wu, G., and El-Deiry, W. Apoptotic death of tumor cells correlates with chemosensititvity, independent of p53 or bcl-2. Clin Cancer Res, 2: 623-633, 1996.

40. Oyaizu, H., Adachi, Y., Yaketani, S., Tokunaga, R, Fukuhara, S., and Ikehara, S. A crucial role of caspase 3 and caspase 8 in paclitaxel-induced apoptosis. Mol Cell Biol Res Commun, 2: 36-41, 1999.

41. Bullrich, F., Fernandes-Alnemri, T., Litwack, G., Alnemri, E. S. and Croce, C. M. Chromosomal mapping of cell death proteases CPP32, MCH2, and MCH3, Genomics 36 (2), 362-365, 1996.

42. Fernandes-Alnemri, T., Litwack, G. and Alnemri, E. S., CPP32, a novel human apoptotic protein with homology to *Caenorhabditis elegans* cell death protein Ced-3 and mammalian interleukin-1 beta-converting enzyme J. Biol. Chem. 269 (49), 30761-30764, 1994.

43. Juan, T. S., McNiece, I. K., Argento, J. M., Jenkins, N. A., Gilbert, D. J., Copeland, N. G. and Fletcher, F. A., Identification and mapping of Casp7, a cysteine protease resembling CPP32 beta, interleukin-1 beta converting enzyme, and CED-3, Genomics 40 (1), 86-93, 1997.

Although the present invention has been described in detail with reference to examples above, it is understood that various modifications can be made without departing from the spirit of the invention. All cited patents, patent applications, publications and other documents cited in this application are herein incorporated by reference in their entirety.

TABLE 1

| IC-50 Values for Ovarian Carcinoma Cell Lines | | |
|---|---|---|
| Cell Line | Carboplatin (mg/ml) | Paclitaxel (nM) |
| CP70 | 75.7 | 18.6 |
| HEY | 45.3 | 100 |
| A2780 | 3.4 | 43.7 |

Table 1: Clonogenic assays were performed on three ovarian carcinoma cell lines exposed to various concentrations of either carboplatin or paclitaxel as described in Methods. IC-50 values were calculated from the survival curves.

TABLE 2

Distribution of Apoptotic Response

| Drug | Number of Cases | |
|---|---|---|
| | Sensitive | Resistant |
| Carboplatin | 21 | 1 |
| Paclitaxel | 10 | 12 |
| Carboplatin and Paclitaxel | 10 | 1 |

Table 2: Three established ovarian cancer cell lines and 19 ovarian cancer patient-derived cell samples were assayed for caspase-3 activity after exposure to either carboplatin or paclitaxel. Increased activity relative to untreated samples was counted as sensitive. All cases that were sensitive to paclitaxel were also sensitive to carboplatin. Only one case was resistant to both drugs.

TABLE 3

Comparison of Clinical Sensitivity to In Vitro Sensitivity

| | Clinically Chemo-sensitive | Clinically Chemo-resistant |
|---|---|---|
| In vitro sensitive to Paclitaxel and carboplatin | 5 | 1 |
| In vitro sensitive to only one agent or neither agent | 2 | 5 |

Table 3: The in vitro response to carboplatin and paclitaxel of 13 samples of tumor cells from ovarian cancer patient ascites fluid was compared to the clinical response of the patients to the same drugs. In vitro sensitivity was defined as an increase in caspase-3 activity relative to untreated samples. Clinical chemotherapy sensitivity was defined as no evidence of disease recurrence for 6 months following the completion of the chemotherapy regimen.

I claim:

1. A method of predicting a clinical response of an epithelial tumor or cancer to chemotherapeutic agents in a patient comprising:
   (a) culturing malignant epithelial cells having an unknown chemosensitivity profile from a patient tumor, ascites fluid, or pelvic washing;
   (b) contacting the malignant cells with said agents separately in vitro; and
   (c) detecting the level of caspase-3 activity induced by each agent, wherein induction of caspase-3 activity in vitro is indicative of chemosensitivity of the tumor or cancer cells in vivo, thereby predicting a clinical response to said chemotherapeutic agents.

2. The method of claim 1, wherein said tumor or cancer cells are epithelial ovarian cancer cells.

3. The method of claim 1, wherein said tumor or cancer cells are cultured to about 50-70% confluency before said contacting.

4. The method of claim 1, wherein said sample is contacted with said agents for about 4 hours to about 48 hours.

5. The method of claim 1, wherein said agents comprise one or more of carboplatin, paclitaxel, docetaxel, gemcitabine, topoteca, and cisplatin.

6. The method of claim 1, wherein caspase-3 activity is detected over a range of drug doses.

7. The method of claim 1, wherein caspase-3 activity is detected over time.

8. The method of claim 1, wherein the cancer is an epithelial ovarian cancer, and the chemotherapeutic agents include carboplatin and paclitaxel.

* * * * *